United States Patent
Alt et al.

[11] Patent Number: 5,578,062
[45] Date of Patent: Nov. 26, 1996

[54] DEFIBRILLATOR SHOCK TIMING IN FIBRILLATORY CYCLE INTERVAL

[75] Inventors: Eckhard Alt, Ottobrunn, Germany; Lawrence J. Stotts, Lake Jackson, Tex.

[73] Assignee: Intermedics, Inc., Angleton, Tex.

[21] Appl. No.: 425,052

[22] Filed: Apr. 19, 1995

[51] Int. Cl.⁶ .................................................. A61N 1/362
[52] U.S. Cl. ................................................................ 607/5
[58] Field of Search ..................... 607/4, 5, 6, 7

[56] References Cited

U.S. PATENT DOCUMENTS

| | | |
|---|---|---|
| 3,805,795 | 4/1974 | Denniston . |
| 4,108,148 | 8/1978 | Cannon . |
| 4,384,585 | 5/1983 | Zipes . |
| 4,996,984 | 3/1991 | Sweeney . |
| 5,048,521 | 9/1991 | Pless . |
| 5,086,772 | 2/1992 | Larnard . |
| 5,099,838 | 3/1992 | Bardy . |
| 5,184,615 | 2/1993 | Nappholz . |
| 5,205,283 | 4/1993 | Olson . |
| 5,275,621 | 1/1994 | Mehra ............................. 607/5 |
| 5,282,836 | 2/1994 | Kreyenhagen .................. 607/4 |

*Primary Examiner*—William E. Kamm
*Assistant Examiner*—Scott M. Getzow
*Attorney, Agent, or Firm*—Wigman, Cohen, Leitner & Myers, P.C.

[57] ABSTRACT

A defibrillator has a signal generator implemented to deliver output shock waveforms and housed in a case adapted to be implanted in the left pectoral region of a cardiac patient. The case is implemented to interact with internal circuitry of the generator to maintain the case active as an electrode. An electrical transvenous lead has a proximal electrode for electrical connection to the internal circuitry of the signal generator and a distal end adapted to be positioned in the right ventricle (RV) of the patient's heart. The lead includes a sensing tip for contacting the RV to sense the patient's ECG signal and a shocking coil arranged to be located in the RV when the transvenous lead is implanted in the patient. The internal circuitry of the signal generator includes triggerable output circuit for developing an output shock waveform when triggered in response to detection of ventricular fibrillation of the patient's heart from the sensed ECG signal. The internal circuitry also includes a timer responsive to the sensed ECG signal for timing the application of the shock waveform developed by the output circuit across the transvenous lead and the active case with a predetermined delay relative to the occurrence of an R-wave of the sensed ECG signal next following detection of fibrillation until at least about 50% of the R-R cycle length of the ECG signal has elapsed, to optimize the timing of delivery of an electric field vector derived from the shock waveform across a myocardial mass of the patient's heart between the shocking coil and the active case.

20 Claims, 1 Drawing Sheet

DEFIBRILLATOR SHOCK TIMING IN FIBRILLATORY CYCLE INTERVAL

BACKGROUND OF THE INVENTION

The present invention relates generally to implantable medical devices, and more particularly to improved implantable cardioverter/defibrillator devices for providing greater efficiency, safety and energy conservation by delivering a defibrillating shock waveform to the implant patient's fibrillating heart at a time of substantially lowest defibrillation threshold (DFT).

Implantable defibrillators are intended to detect events of fibrillation quickly and accurately, and to respond rapidly with an effective defibrillation therapy. Typically, these types of devices are designed to detect pathologic tachycardia and fibrillation events, and, in response, to initiate delivery of an electrical shock waveform (sometimes referred to herein simply as "shock") of appropriate energy and shape to cardiovert or defibrillate the patient's heart accordingly.

Clearly, it is important in the case of any implantable, battery-operated medical device to provide design and operation for energy conservation within the constraints of its therapeutic function to enable sufficient energy reserve for a reasonable lifetime of the device, and to allow for a reduction in size and weight to the lowest possible level. This is particularly important for automatic defibrillators, which may be required to expend comparatively large amounts of energy each time an episode of actual or imminent fibrillation is detected. The aim is that the designated therapy be delivered at a point in time adequate for successful termination of the dysrhythmia, to return the heart to normal sinus rhythm with the least expenditure of energy. Generally speaking, the optimum time for delivering a defibrillating shock is when the DFT is likely to be lowest within a suitable window of earliest opportunity. There is no value to a quest to save energy which imposes a waiting time that could cost the patient's life.

U.S. Pat. No. 4,384,585 to Zipes describes synchronous cardioversion in which the possibility exists to induce fibrillation by non-synchronous shocking. The synchronous cardioversion is intended to deliver the shock at a time when the bulk of the cardiac tissue is depolarized and in a refractory state. Non-synchronous cardioversion is sought to be avoided to preclude delivery of cardioverting energy during the vulnerable T-wave portion of the cardiac cycle. The patient's electrogram is used to detect depolarizations of the cardiac tissue and to produce a corresponding sense signal. Additional detection criteria are applied to determine whether a tachyrhythmia is present. The detection circuitry determines the time interval between successive cardiac depolarizations, and initiates a discharge of energy stored in an output storage capacitor if either the average detected heart rate is above a preset threshold for a specified period of time or the rate accelerates by a preset amount. Alternatively, the device detects a departure of selected beats from a historic data base of successive R-R intervals stored in the device memory; or performs a waveform analysis of the electrogram information with pattern recognition of time domain or frequency domain characteristics of the tachyrhythmia signal. The shock is delivered synchronously with the occurrence of an R-wave after specified criteria are met.

U.S. Pat. No. 4,996,984 to Sweeney describes a defibrillation technique in which fibrillation cycle length (average time interval between successive depolarizations) is measured and therapy is delivered in the form of multiple bursts of electrical current timed according to that cycle length. When cardiac tissue cells are activated, the normal electrical gradient constituting the voltage difference within and outside the cell collapses, or depolarizes. The depolarization propagates from cell to cell, the collapse of each initiating the collapse of the next in a moving wavefront. As a cell is depolarized it immediately begins repolarization to reestablish a voltage difference sufficient once again for depolarization, during the course of which the tissue is refractory. During the refractory period, the cell is incapable of responding to a stimulus. According to the multiple burst defibrillation technique of the '984 patent, the successive bursts are timed to occur at successive depolarizations at a designated site in the myocardium, so that the time interval between bursts is adjusted to correspond to the fibrillation cycle length. The cycle length is determined using cross-correlation, auto-correlation, fast Fourier transformation, counting R-waves of the electrocardiogram over a fixed time period, and determining the R-R intervals of individual cardiograms.

An improved technique for timing the delivery of defibrillating shocks is disclosed in co-pending patent application Ser. No. 310,281, filed Sep. 14, 1994 ("the '281 application") of the same applicants as in this case, commonly assigned herewith. The implanted device delivers the cardioverting or defibrillating therapy to the implant patient's heart timed for rapid and successful termination of a dysrhythmia in an energy efficient manner. To that end, changes are observed in characteristics of the patient's cardiac activity during fibrillation, such as amplitude and frequency of the ECG signal detected by intracardiac, transthoracic, or surface type techniques. The discrete ECG signal detected during fibrillation from intracardiac electrodes, for example, indicates the status of excitability or nonexcitability of the major parts of the heart. As the cardiac activity undergoes several fibrillatory cycles, a major fibrillation wavefront was found to drive the muscular masses through a regular cellular cycle of depolarization and repolarization, with the result that different masses of the heart have different status of absolute refractoriness, relative refractoriness and full excitability. It was determined that this regular cycle of the cells in a particular mass of tissue of the fibrillating heart (or with activity closely related thereto, such as an accelerating pathologic tachycardia or flutter) can serve to identify a point in the fibrillation cycle at which the heart has the lowest DFT and is therefore most susceptible to defibrillation by application of a relatively low energy shock.

In essence, the amplitude and frequency of the intrinsic ECG signal of a fibrillating heart undergo change according to a regular cycle which is detectable from the ECG wave envelope (e.g., by an intracardiac technique), as the major fibrillation wavefront propagates, so that the defibrillating shock may be timed for synchronous application at or near the point in time of highest amplitude of the ECG signal and lowest frequency of discrete intracardiac potentials, consistent with lowest DFT.

In an embodiment disclosed in the '281 application, detection criteria employed by the implanted device are used to sense imminent or ongoing fibrillation. At that time, the output storage capacitor(s) of the device commence charging, and while the charging is underway the phasic variations in amplitude and frequency of the patient's ECG are detected by pattern recognition, in preparation for timing the delivery of a shock waveform from the capacitor(s) at the optimum point in the regular cellular cycle of the cardiac activity. After a sufficient number of successive intervals of high amplitude, low frequency cardiac activity have been observed to indicate a trend, the capacitor(s) are discharged to deliver a shock at the very next interval of increasing amplitude of the ECG signal, i.e., in substantial synchronism with a point of increasing amplitude of the intrinsic ECG signal and decreasing frequency of discrete depolarizations. The scanning of cardiac events is conducted over a search period of sufficient length to identify an optimum point in the cycle for delivery of the shock. The optimum point may occur where either or both of the amplitude of the intrinsic ECG signal and the interval between occurrences (i.e., reciprocal of frequency) of intracardiac discrete ECG depolarizations are increasing. Both parameters may be increasing, or only one, but the desire is to trigger the shock at a point where the ECG signal amplitude is likely to be greatest. The device may be implemented to calculate the quotient of amplitude over frequency to ascertain optimum timing.

It is the principal aim of the present invention to provide further improvements in methods and devices for timing the delivery of defibrillating shocks to achieve successful defibrillation rapidly and with relatively low energy.

SUMMARY OF THE INVENTION

As noted above, it has been traditional upon observing an event of ventricular fibrillation (VF) to apply the defibrillating shock(s) synchronous with the occurrence of an R-wave or a signal indicating an ongoing action potential at the site of the sensing electrode. With transvenous defibrillation, the shocking coil incorporates both sensing at the tip of the electrode and the coil. True integrated bipolar sensing therefore provides a measurement of local activity of the heart. Despite previous assumption that a chaotic state exists when the heart is in VF, measurements performed by the applicants have evidenced a considerable degree of organization within the ventricle during fibrillation. Applicant's studies have shown that, realistically, as much as 65% of the muscle cells of the myocardium undergo an organized depolarization and repolarization. The occurrence of the R-wave at the site of the electrode indicates that the cells at this local site are undergoing depolarization. By measurement of the R-R or fibrillatory cycle length, i.e., the time interval between successive R-waves (referred to herein simply as cycle length), one can determine the wavelength of this wavelet if the speed of conduction is known. Typically, wavelets occurring during VF have cycle lengths ranging from about 180 to 250 milliseconds (ms) with a mean of about 220 ms.

Synchronizing delivery of the shock with occurrence of an R-wave is less than optimum, because the local portion of the heart constituting the detection site is undergoing depolarization at that time. Thus, a shock delivered to that site within the upstroke or refractory period of this very localized myocardial area will not serve to trigger any event. But it is of critical importance to reset areas of the heart relatively remote to that site with the shock to resynchronize the depolarization and repolarization process. Dispersion of the repolarization or lack of resynchronization is the major cause of the inability to defibrillate the heart.

The applicants have found that a shock applied in the relative refractory period, which lies in an interval from about 75% to about 90% of the cycle length, can considerably prolong the action potential induced following the shock. Other portions of the heart currently undergoing an initial upstroke would also be reset by the shock with such timing.

Additional findings have indicated that it is better to apply an anodal (positive) shock into this period of refractoriness at the local site. It is known that thresholds with an anodal stimulus are about 1½ to 2 times higher than with a cathodal stimulus applied close to the stimulation site. But since the electric field strength in the vicinity of the shocking coil far exceeds the threshold (it is assumed that voltage gradients in a range from 60 to 70 volts are generated close to the electrode), the anodal voltage strength is sufficient to depolarize the locally adjacent myocardium. The more remote parts of the heart (from that site) require a higher field strength to achieve depolarization, which can be achieved by a cathodal shock. Significantly, these more remote portions of the heart are in closer proximity to the cathode, such as if the cathode is located at or near the left side of the heart. For example, an active case (i.e., the metal housing of the signal or shock generator implemented as an electrode) may be employed with unipolar or bipolar configurations. With these findings in mind, according to the present invention, the shock energy needed for defibrillation can be decreased by 10 to 20% (relative to the prior art techniques) if the shock is timed to be applied within the last half of the fibrillatory cycle, and preferably at a point from about 75% to about 90% of the cycle length, and further, if this shock is anodal (of positive polarity) at the time of application to the tissue at or very near the site where the defibrillation coil is located.

High gradient areas are located close to the defibrillating electrodes, and low gradient areas are at sites distant from the electrodes. It has been shown that most defibrillation shocks—successful or not—appear to halt activation waveforms during VF. Unsuccessful shocks are usually followed by reentry, resulting in refibrillation. Moreover, the earliest activation front following an unsuccessful defibrillation shock tends to occur in areas of low potential gradients. Since the areas more remote from the defibrillation coil are the points where the critical field is more difficult to establish, an anodal polarity for the electrode positioned in the right ventricle (RV) is superior for lower DFT if the shock is applied within the relative refractory period of the myocardium closest to the defibrillation coil. Additionally, this lower field strength following an anodal shock diminishes the risk of refibrillation following spontaneous ectopic, post-shock activation originating from areas of high potential gradients most likely to be very close to the area where the RV electrode is located.

Therefore, another aim of the present invention is to provide an implantable cardioverter/defibrillator in which optimum timing of delivery of the prescribed electrical shock to a patient's heart is achieved, with high reproducibility of performance.

A more specific object of the invention is to provide a method for reducing the level of energy required to be delivered in a successful defibrillating shock from an implanted cardioverter/defibrillator by initiating the shock to be applied starting in the latter part of the fibrillation cycle length, and with positive polarity (at least of the initial phase in the case where a multiphasic, as opposed to a monophasic shock waveform is used).

Another important aspect of the invention is to enable reduction of defibrillation energy requirements so as to allow the design and use of implantable defibrillators of smaller size and lighter weight than was heretofore achievable.

BRIEF DESCRIPTION OF THE DRAWINGS

The above and other objects, aspects, features and attendant advantages of the invention will be recognized from the following detailed description of a preferred embodiment and method constituting the presently considered best mode of practicing the invention, in conjunction with the accompanying drawings, in which.

DESCRIPTION OF THE PREFERRED EMBODIMENT AND METHOD

Figure 1:
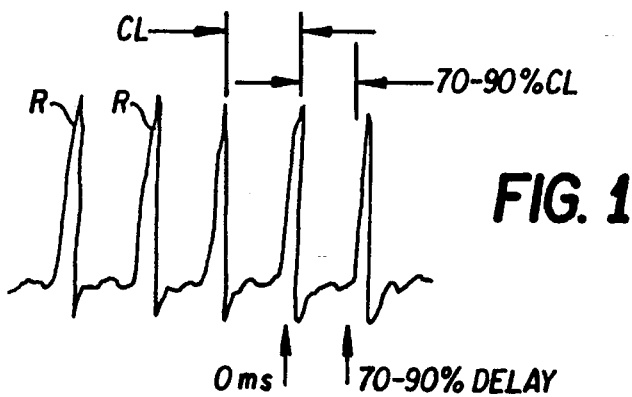
FIG. 1 is a generalized intracardiac waveform illustrating detection of peak energy coincident with the occurrence of the R-wave at the detection site during an episode of VF.

In general, the device operates to recognize a dysrhythmia, specifically pathologic tachycardia or fibrillation of the ventricle, by use of known, conventionally applied internal detection criteria. When these criteria are fulfilled, the device looks at whether the cardiac signal indicates ongoing tachycardia or fibrillation, and, after applying an appropriate electrical therapy regimen, whether sinus rhythm is restored. If the criteria for fibrillation are satisfied, the device is conditioned to react by immediately initiating charging of its shocking capacitor(s).

As observed in the background section above, in the device and method disclosed in the '281 application, the patient's intracardiac ECG signal is scanned during a ventricular fibrillation (VF) event for the highest amplitude and lowest frequency areas within the fibrillatory cycle as the best time to apply the shock. In the art prior to that disclosure, the shock delivery was triggered for synchronization with occurrence of any R-wave or a depolarization signal when sensed from the ventricle. Earlier versions of implantable defibrillators simply applied a shock at any time that VF was detected, without any attempt to synchronize the delivery with a particular point in the cardiac cycle. The '281 application observed that despite an ongoing event of VF, organized intracardiac signals are present which can be sensed and which contribute to the diagnosis of VF.

Thus, although it had previously been assumed that fibrillation was characterized by a chaotic current throughout the heart, an underlying organized cardiac activity is actually present representing more than the local phenomenon, whose rhythm can be detected with the intracardial electrode. The wavelet of this underlying rhythm repeatedly runs through the heart and returns, with a wavelength constituting the time interval between consecutive R-waves (the cycle length typically running on the order of 180 milliseconds up to about 250 ms).

The R-wave may be detected using an intracardial electrode, and in present-day transvenous lead systems that electrode is located on the same lead or otherwise very near the shocking coil electrode in the right ventricle. Therefore, the R-wave is detected at a myocardial site of the heart at which depolarization is taking place, and if synchronous delivery with the R-wave is employed the greatest concentration of the shock energy will be applied into that same site.

The surface ECG has a very close correspondence in cycle length to the intracardial ECG. Additionally, the intracardiac signals are found to have an average amplitude of about 10 millivolts (mv) during VF, compared to about 15 mv during sinus rhythm. This may be a local phenomenon, but with surface ECG detection the signal amplitude during VF is also in the range of about 50% to about 70% of the amplitude during sinus rhythm. The amplitude of the ECG is affected by two factors: 1) the myocardial mass, according to the number of fibers that depolarize; and 2) the vector of the electric field in the region of the detection. If the vector runs parallel to the bipolar lead, maximum amplitude is detected because first the ring and then the tip of the lead is excited. If the vector runs perpendicular, however, both ring and tip are excited at the same time, resulting in no difference in potential being detected between the two.

Experiments conducted by the applicants indicate that approximately from 50% to 70% of the heart still experiences organized depolarization and repolarization cycle during VF. If a defibrillating shock is applied in synchronism with the detected R-wave, the highest energy density will be delivered to or very the same site at which the R-wave is being detected, and hence, at which the muscle cells are already depolarized. But in that case no reset is necessary at that location, so this is wasteful of precious energy and unlikely to terminate the VF.

The success of depolarization is dependent on the dispersion of refractoriness of repolarization, i.e., a cell depolarizes, maintains that status for a time, and then repolarizes. To break the VF, it is essential that all cells should be synchronized to the same repolarizing cycle. It should not be concluded from the measurements, however, that the dispersion of the refractoriness indicates whether the shock is successful or not. Rather, the phase shift of the occurrence of the depolarizations at different portions of the ventricle is the underlying cause.

In dog tests conducted by the applicants, different shock timing schemes were employed to defibrillate the heart in VF, in which the shock was triggered synchronous with the R-wave (or with signals indicating a local action potential) in one test; with a 50 millisecond (ms) delay following the R-wave in another test; with a 100 ms delay in still another test; and with a 150 ms delay in yet another. Additionally, the delay intervals were selected to coincide with about 25%, 50%, and 75%, respectively, of the R-R cycle length. It was found that initial delivery of a shock of positive polarity (so that the coil electrode was acting as the anode) applied into the relatively refractory period of an R-wave next following the detection of fibrillation resulted in defibrillation at an energy level markedly less than that required for a shock applied synchronous with the R-wave. Indeed, the reduction exceeded 15%; for example, 15.4 joules was required versus 11.8 joules in one set of tests using a carbon electrode, and 14.1 versus 12.6 in another set. While this cannot be characterized as an extremely great difference, the trend is significant with respect to both energy and voltage, with a positive stimulus.

The present invention therefore constitutes a significant improvement over the shock timing techniques regularly employed in prior art implanted defibrillator devices, in both energy reduction and likelihood of earlier success. It also represents an advance over the technique disclosed in the '281 application, in that the latter technique requires at least a limited expenditure of time to conduct a search for the point or span of the cardiac activity having the desired characteristics of amplitude and frequency, at which a shock is to be applied. In contrast, the present invention designates the optimum time for application of a shock within milliseconds of the R-wave, as well as being concerned with the polarity selected for the shock.

It turns out that at from 50% to 100%, and preferably from 75% to 90% of the R-R cycle length (typically, at or near the end of the repolarization cycle), a positive polarity shock applied into the relatively refractory tissue provides considerably better results than cathodal-induced depolarization of the same stimulus strength. Full depolarization occurs at about 85% of the cycle length. Because it is usually more difficult to stimulate a cell with a positive (anodal) stimulus than with a negative (cathodal) stimulus, by tradition it is preferable to apply a cathodal pulse to the tissue for stimulation, as in the case of cardiac pacing. But in view of our findings, at the late stages of the repolarization cycle it is more efficient to utilize positive hyperpolarization, at least at initiation of the delivery. Moreover, the tissue more remote from the shocking electrode site is more responsive to cathodal stimulation (the wavelet circulating so that depolarization is occurring at those locations), which is ideal because the cathode is generally placed closer to these remote sites.

A key aspect of the present invention, then, is that the shock is timed to be delivered a predetermined (i.e., programmed) fixed delay interval after the R-wave occurs at the intracardial electrode site. It is desirable that the programmed delay causes the shock to be applied to the heart at a fixed point in the latter 50% of the R-R cycle length. Another important aspect of the invention is that the polarity of the shock at the time of initial application is selected to be positive for application during that preferred portion of the cycle length (and, indeed, at any point in the cycle having a substantial delay relative to the R-wave), in contrast to application synchronous with or only slightly displaced from the R-wave where a shock of negative polarity would be preferable. For a monophasic shock waveform, at least substantially the entire delivery would be of positive polarity, whereas for a biphasic waveform, the positive portion would be applied in the first phase and the negative portion in the second phase.

Preferably, the RV defibrillation electrode is juxtaposed for delivery of the shocks with the active case or "active can" of the signal generator (sometimes referred to as the therapy generator, pulse generator, shock generator, or stimulus generator) of the defibrillator, which, with the shock waveform having that polarity, acts as the cathode when the former is the anode.

Any of three possible mechanisms may cause a shock to fail. First, the minimum voltage gradient or field gradient required in 90% of the myocardial muscle cells may not be reached everywhere, i.e., some areas have low field gradient and cannot be reset. Second, some areas may need a higher field gradient than others, such as where the patient is on medication or has a disorder that imposes the need for a higher minimum field gradient. Third, and a frequent cause of re-fibrillation, is that the voltage gradient close to the electrode is so high that fibrillation is reinitiated starting from the site where the shock was applied.

To achieve a more equal distribution, the polarity and pulse width of the shock should be adapted to the impedance and capacitance of the device to avoid mismatches. For a biphasic shock, it is preferred not only that the first phase have positive polarity, but that it be of greater duration than the second phase. Also, several optimizing factors may be combined to lower the defibrillation threshold (DFT). For example, optimal shock timing as advanced by the present invention provide a 15% or greater reduction, while the use of carbon electrodes can provide another 5% to 10%, and an optimal waveform shape can give yet another 5% to 10%, so that the total effect yields a quite considerable reduction in DFT. Of equal or perhaps even greater importance, these combined factors can serve to eliminate the large variations in DFT sometimes encountered not only in different patients but in the same patient. For example, in one episode of VF the patient may need a 30 joule shock for successful defibrillation, and yet only a 12 joule shock may be required to terminate fibrillation on the very next VF event in the same patient, or vice versa.

According to the laws of electrophysiology, either an electric field (produced, for example, by a shock waveform applied at a selected site of the heart) is strong enough to depolarize a single myocardial cell or it is not—there is no middle ground. Therefore, any excess over that amount of energy required for depolarization serves no useful purpose in depolarizing the cell, and indeed, may be injurious. There is a critical value, which has no relation to the timing of the shock delivery. The DFT relates to the energy threshold at which the cells representing a critical mass depolarize. As noted, however, DFT can vary considerably at different times within the same patient, which may relate more to underlying changes in the morphology or pattern of the fibrillation, i.e., certain regions of the myocardium may be easier to defibrillate at any given moment than other regions.

In a preferred embodiment of the invention, a peak detector is used to sense R-waves during VF. As illustrated in FIG. 1, the R-waves occur with considerable regularity despite ongoing fibrillation. The cycle length (CL) is shown as the interval between these R-wave peaks. If, for example, a delay in application of the shock relative to occurrence of an R-wave were desired to coincide with a point at about 75% of the CL, the delay would be about 150 ms for the "average" CL of 200 ms.

Figure 2:
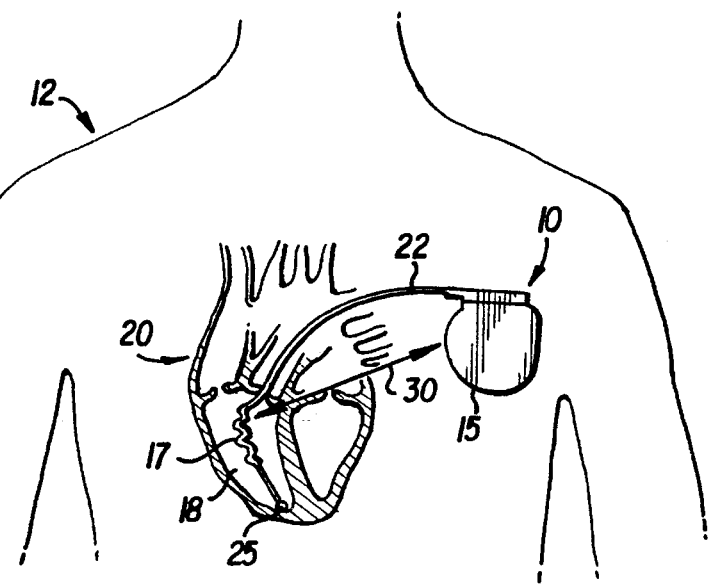
FIG. 2 is a diagram of a defibrillator implanted in a patient, illustrating the location of the sensing electrode and shocking coil in the right ventricle and of the shock generator with active case positioned in the patient's chest.

Referring now to FIG. 2, the signal generator 10 is preferably implanted in the left pectoral region of the cardiac patient 12. The conductive case 15 of the generator is electrically connected to the internal circuitry to render the case "hot", or active. That is, the case is to be utilized as an electrode for purposes of interaction with the defibrillation coil electrode 17 located in the right ventricle 18 of the patient's heart 20 when the transvenous lead 22 is implanted. At the distal tip of the transvenous lead, a sensing electrode 25 is positioned in contact with or immediately adjacent the myocardial tissue at the apex of the ventricle to detect the electrical intracardiac activity occurring at that site.

The distal tip electrode 25 and the shocking coil electrode 17 are so close to one another that, for practical purposes, the greatest electric field strength, when an electrical shock waveform is applied to the transvenous lead, will be present at the same site at which an R-wave is detected by the sense electrode. With an active case for the signal generator, the electric field vector 30 is in the direction from the RV shocking coil to the case, so that the field encompasses a substantial part of the ventricular myocardial mass of the heart, diminishing with distance from the coil electrode. If the shock is applied to make the coil the anode and the case the cathode, as is preferred, the positive polarity exists at the myocardial cells proximate the coil, while cells most remote from that site are closer to the generator case and therefore experience negative polarity of the field. This is highly desirable for reasons pointed out above.

Figure 3:
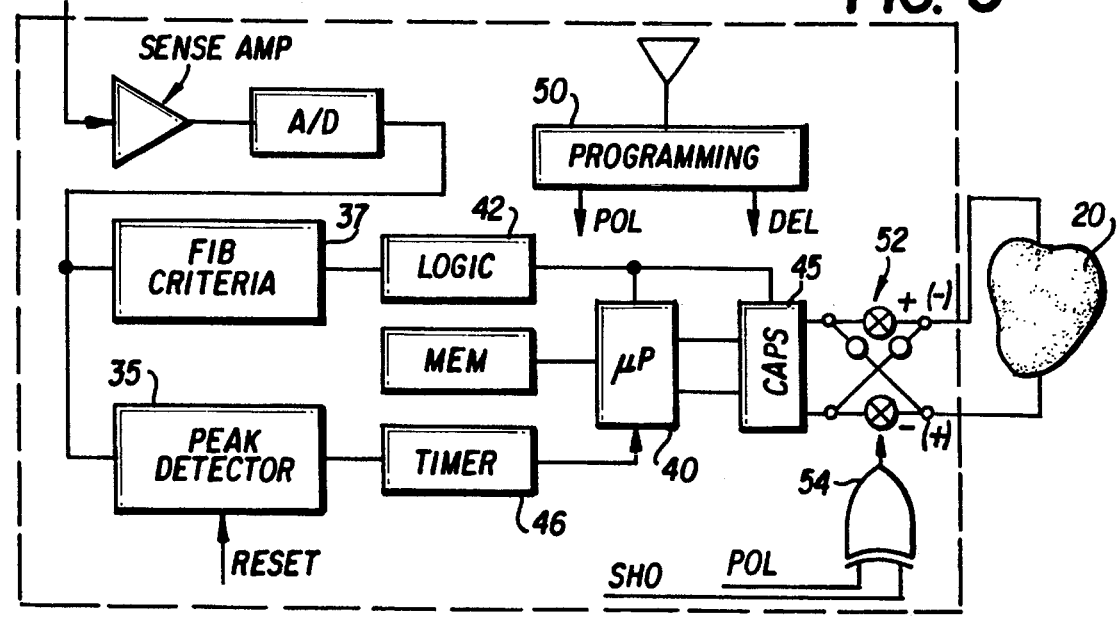
FIG. 3 is a simplified diagram of a portion of the circuitry of the implantable defibrillator employing the principles of the present invention.

The shock waveform circuit, shown generally in FIG. 3, includes a peak detector 35 for detecting the R-wave, in addition to conventional fibrillation detection means 37 which is typically encompassed by software establishing certain criteria indicative of fibrillation and tested in conjunction with an internal microprocessor 40. When the fibrillation criteria are fulfilled, associated logic 42 indicates that the heart 20 is in fibrillation, which results in a command to an output storage capacitor circuit 45 to commence charging the capacitor(s). Alternatively, the capacitor(s) may be charged at any time that a pathologic tachycardia is detected to be rapidly accelerating and thus likely to induce fibrillation, in the interests of saving time to achieve an appropriate magnitude for a defibrillating shock.

A full charge takes a certain time interval that depends on the energy required and the type and size of the capacitor(s) involved. Typically, the charging interval is five to eight seconds. In a conventional manner, the signal generator circuitry (including software) may be implemented to perform a recheck during the charging cycle to verify the existence of fibrillation. If verification is obtained, the device is then ready to deliver an output shock waveform on receipt of an instruction to do so, its capacitor(s) by that time being at "full" charge. If, however, the recheck fails to verify fibrillation, the charging cycle can be aborted. False shocking is not only painful to the patient, but wasteful of battery energy that should be conserved to the greatest practicable extent.

For purposes of the present invention, the generator circuitry includes a timer 46 that times out after a set interval following detection of the R-wave during fibrillation, to provide the predetermined delay (in ms) which will place the shock in the desired portion of the cycle length. The detected R-wave triggers the timer, which initiates a programmed delta from that point. Preferably, both the delay interval and the polarity of the shock (monophasic, or first phase of a biphasic shock) are programmed into the device by conventional techniques using an external programmer (not shown) at the time of or immediately after the device is implanted. For the sake of convenience, this function is provided by the internal block 50 labeled "programming."

Polarity of the shock may be designated, by programming or in conjunction with an algorithm or by any other conventional means, to be negative if initiated in the first quarter or half of the R-R cycle length, and positive if initiated at any other time in the cycle. By way of example, a simple bridge circuit 52 is illustrated to effect a positive polarity shock when triggered after a delay interval (in ms) that causes the shock waveform to be applied across the coil electrode of the transvenous lead and the active case during any part of the last half of the cycle length, and to effect a negative polarity shock when triggered in the first half of the cycle length (or for the second phase of a biphasic shock waveform). To that end, a + or − instruction is delivered to a switching circuit from logic including an exclusive OR gate 54 so that if the instruction level is high the polarity is of one type and if low an inversion occurs to make the polarity of the other type, and the output shock is delivered (with the programmed delay) accordingly to the heart. For biphasic shocking pulses, the phases may also be programmable to make the second phase shorter, of equal length, or longer than the first phase, although preferably, the first phase is the longer.

The shock timing of the invention is maintained irrespective of the particular lead configuration. It would not matter, for example, if electrodes are positioned in RV and superior vena cava (SVC) configuration, or RV to an active case, or if patches or other configurations are employed. Also, the polarity of the shock, and of the electrodes, as taught herein is not limited to a particular electrode configuration. Polarity may be selected not only with the above factors in mind, but also may take into account the clinical situation, i.e., the underlying disease of the patient. Here again, the circuitry is preferably such that both polarities are available, and programmable for selection according to which is most beneficial to the particular patient after testing, and on the basis of lowest DFT.

Therefore, although certain preferred embodiments and methods have been disclosed herein, it will be appreciated by those skilled in the art to which the invention pertains, that variations and modifications of these embodiments and methods may be readily implemented without departing from the spirit and scope of the invention.

What is claimed is:

1. A defibrillator comprising:

a signal generator including internal circuitry implemented to deliver output shock waveforms and housed in a case adapted to be implanted in the left pectoral region of a cardiac patient, wherein the case is implemented to interact with the internal circuitry of the generator to maintain the case active as an electrode, an electrical transvenous lead having a proximal electrode for electrical connection to the internal circuitry of the signal generator and a distal end adapted to be positioned in the right ventricle (RV) of the patient's heart and including a sensing tip for contacting the RV to sense the patient's ECG signal and a shocking coil arranged to be located in the RV when said transvenous lead is implanted in the patient, the internal circuitry of said signal generator including triggerable output means for developing an output shock waveform when said output means is triggered in response to detection of ventricular fibrillation of the patient's heart from the sensed ECG signal, and timing means further responsive to the sensed ECG signal for timing the application of the shock waveform developed by said output means across said transvenous lead and said active case with a predetermined delay relative to the occurrence of an R-wave of said sensed ECG signal next following said detection of fibrillation until at least about 50% of the R-R cycle length of the ECG signal has elapsed, to optimize the timing of delivery of an electric field vector derived from the shock waveform across a myocardial mass of the patient's heart between the shocking coil and the active case.

2. The defibrillator of claim 1, wherein said timing means includes polarity designating means for designating the polarity of said shock waveform according to the extent of the predetermined delay imposed on the application of the shock waveform relative to the occurrence of an R-wave.

3. The defibrillator of claim 1, wherein said timing means includes polarity determining means responsive to said delay exceeding 50% of the R-R cycle length of the ECG signal for causing said shock waveform to be initiated with positive polarity and applied to render the shocking coil as the anode and the active case as the cathode.

4. The defibrillator of claim 1, wherein said timing means is programmable to delay the application of the shock waveform across said transvenous lead and said active case by a predetermined time interval in the range from about 75% to about 90% of the R-R cycle length.

5. The defibrillator of claim 4, wherein said internal circuitry further includes polarity designating means responsive to a delay in application in said range for initiating said shock waveform with a positive polarity so that the shocking coil acts as the anode in said delivery of the electric field vector.

6. The defibrillator of claim 4, wherein said triggerable output means comprises means for developing an output shock waveform with a biphasic morphology with a second phase of shorter duration than the first phase, and a polarity such that the shocking coil is the anode during application of the first phase of the shock waveform.

7. The defibrillator of claim 1, wherein said timing means comprises means for timing the application of the shock waveform across said shocking coil and said active case with a programmable delay relative to occurrence of the R-wave next following detection of ventricular fibrillation.

8. An implantable defibrillator comprising stimulus generator means for selectively generating an electrical shock output, a conductive case housing said stimulus generator means and connected electrically to circuitry within the stimulus generator means to render the case electrically active as an electrode, detection means within the circuitry of the stimulus generator means for sensing ventricular fibrillation (VF) from cardiac activity of a patient in which the defibrillator is implanted and for initiating the generation of said electrical shock output in response to the sensing of VF, and timing means within the circuitry of the stimulus generator means responsive to the sensing of VF and to the patient's underlying organized cardiac activity for delaying the generation of the electrical shock output of the stimulus generator for a programmed time interval following occurrence of an R-wave after VF is sensed, wherein the time interval is programmed to impose a delay from said occurrence of the R-wave to generation of the electrical shock output of at least about 50% of a period between consecutive R-waves.

9. The defibrillator of claim 8, further including polarity means for setting the polarity of the shock output depending on the extent of the delay imposed by the programmed time interval.

10. The defibrillator of claim 9, wherein the polarity means is implemented to set a positive shock output when the timing means is programmed to delay the generation of the shock output of the stimulus generator for a time interval of at least 100 ms from the occurrence of an R-wave.

11. The defibrillator of claim 8, wherein the stimulus generator means is adapted to generate a shock output having one or more phases of programmed duration and polarity.

12. The defibrillator of claim 8, further including electrical lead means implantable in the patient and having a proximal end with a tip for electrical connection to circuitry within the stimulus generator means through an electrical connector on the case, and having a distal end including an electrical coil and a sensing tip adapted to be disposed within the right ventricle of the patient for communicating cardiac activity of the patient to the stimulus generator means and for communicating the shock output to the right ventricle of the patient.

13. A method for defibrillating a human heart in ventricular fibrillation (VF) which comprises the steps of: sensing VF, sensing the presence of an underlying organized cardiac activity of the heart during VF, developing a shock waveform in response to having sensed VF, delaying application of the developed shock waveform to the heart for a time interval equal to at least about 50% of the entire time period between consecutive R-waves of the underlying organized cardiac activity of the heart, and timing the delay in said application from occurrence of an R-wave.

14. The method of claim 13, wherein the step of delaying application of the shock waveform imposes a delay in the range from substantially 50% to substantially 90% of the R-R cycle length characterized by the time period between consecutive R-waves.

15. The method of claim 13, wherein the delay is set to time the application of the developed shock waveform to occur during a relative refractory period of the R-R cycle length constituting the time period between consecutive R-waves, for tissue at a point of application of the shock waveform.

16. The method of claim 13, further including setting the initial polarity of the shock waveform according to the extent to which the shock waveform is delayed relative to occurrence of an R-wave before application to the heart.

17. A device-implemented method of optimum timing of the delivery of a therapeutic electrical shock to the heart of a patient in which a shock delivery device is implanted, in response to detection by the device of actual or imminent fibrillation of the patient's heart, said method comprising:
monitoring the patient's ECG, and
upon said detection, triggering the delivery of a shock to the heart to be synchronous with a predetermined time delay from occurrence of an R-wave of the ECG which is at least about 50% of a full cycle between consecutive R-waves of the ECG, so that the shock is delivered in a relative refractory period of tissue cells of the heart contributing to said actual or imminent fibrillation, to achieve reproducible, low shock energy defibrillation of the heart.

18. The device-implemented method of claim 17, wherein said triggering is performed so that the shock is delivered to the heart synchronously with expiration of a predetermined time delay in a range from about 75% to about 90% of said full cycle.

19. A defibrillator device adapted to be implanted in a patient for automatic initiation of therapy in response to sensing an ECG signal of the patient's heart indicative of actual or potential fibrillation, comprising:
therapy delivery means responsive to detection of the fibrillation-indicative signal for developing an electrical shock waveform to be applied to the heart to terminate or avoid fibrillation,
detection means for detecting said fibrillation-indicative signal from a predetermined set of detection criteria and, if fibrillation is present, for monitoring a fibrillation cycle associated therewith, and
timing function means further responsive to detection of said fibrillation-indicative signal and monitoring of the fibrillation cycle for timing delivery of the developed electrical shock waveform to the heart at a point in time in said fibrillation cycle which is synchronized with a predetermined delay interval, relative to the occurrence of an R-wave of said cycle, of at least substantially 50% of a time period between consecutive R-waves of said cycle, whereby to enhance the probability of successful termination of fibrillation at a low energy level of said electrical shock waveform.

20. The defibrillator device of claim 19, wherein said timing function means is responsive to detection of said fibrillation-indicative signal and monitoring of the fibrillation cycle for timing delivery of the developed electrical shock waveform to the heart at a point in time in said fibrillation cycle which is synchronized with a predetermined delay interval, relative to the occurrence of an R-wave of said cycle, in the range from substantially 75% to substantially 90% of a time period between consecutive R-waves of said cycle.

* * * * *